US009480537B2

(12) United States Patent
Stadelman et al.

(10) Patent No.: US 9,480,537 B2
(45) Date of Patent: Nov. 1, 2016

(54) SELF POSITIONING TRACHEAL TUBE CLEARANCE MECHANISM USING A COLLAR

(71) Applicant: AVENT, INC., Alpharetta, GA (US)

(72) Inventors: Jennifer S. Stadelman, Alpharetta, GA (US); Joseph A. Cesa, Cumming, GA (US); Carolyn Y. Sargent, Lawrenceville, GA (US)

(73) Assignee: Avent, Inc., Alpharetta, GA (US)

( * ) Notice: Subject to any disclaimer, the term of this patent is extended or adjusted under 35 U.S.C. 154(b) by 564 days.

(21) Appl. No.: 14/026,122

(22) Filed: Sep. 13, 2013

(65) Prior Publication Data
US 2014/0090194 A1     Apr. 3, 2014

Related U.S. Application Data

(60) Provisional application No. 61/707,259, filed on Sep. 28, 2012.

(51) Int. Cl.
*A61B 90/70*     (2016.01)
*A61M 16/04*     (2006.01)
(Continued)

(52) U.S. Cl.
CPC .............. *A61B 90/70* (2016.02); *A61M 16/04* (2013.01); *A61M 16/0434* (2013.01); *A61M 16/0463* (2013.01); *A61M 25/0082* (2013.01); *A61B 2090/701* (2016.02);
(Continued)

(58) Field of Classification Search
CPC .... A61B 90/70; A61B 90/701; A61B 19/34; A61B 19/343; B08B 9/00; B08B 9/02; B08B 9/027; B08B 9/035; B08B 9/04

USPC ............................. 15/104.05, 104.16–104.19
See application file for complete search history.

(56) References Cited

U.S. PATENT DOCUMENTS

| 4,762,125 A * | 8/1988 | Leiman ............. A61M 16/0479 128/207.14 |
| 5,003,657 A * | 4/1991 | Boiteau ............... A61M 1/0078 15/104.16 |

(Continued)

FOREIGN PATENT DOCUMENTS

| DE | 10 2010 026 774 A1 | 1/2012 |
| GB | 2 482 618 A | 2/2012 |

(Continued)

OTHER PUBLICATIONS

Co-pending U.S. Appl. No. 14/026,139, filed Sep. 13, 2013, by Stadelman et al. for "Self Positioning Tracheal Tube Clearance Mechanism Using Whisks.".

(Continued)

*Primary Examiner* — Joseph J Hail
*Assistant Examiner* — J Stephen Taylor
(74) *Attorney, Agent, or Firm* — Dority & Manning, P.A.

(57) ABSTRACT

A device for cleaning the interior wall of a catheter has a cleaning lumen and a non-inflatable removal element comprising a sliding collar that has a first location as the cleaning lumen advances and a second location as the cleaning lumen retracts within the catheter. A sliding collar has a first position when unconstrained and a second position when within the catheter. The removal element self-positions the device concentrically within the catheter. Suction is desirably applied to the cleaning lumen during use.

19 Claims, 2 Drawing Sheets

(51) Int. Cl.
*B08B 9/035* (2006.01)
*B08B 9/04* (2006.01)
*A61M 25/00* (2006.01)

(52) U.S. Cl.
CPC . *A61M 2025/0019* (2013.01); *A61M 2209/10* (2013.01); *B08B 9/035* (2013.01)

(56) References Cited

U.S. PATENT DOCUMENTS

| | | | | |
|---|---|---|---|---|
| 5,143,062 | A * | 9/1992 | Peckham | A61M 16/04 128/207.14 |
| 6,494,208 | B1 * | 12/2002 | Morejon | A61M 1/0078 128/207.14 |
| 6,699,331 | B1 * | 3/2004 | Kritzler | B08B 9/0436 134/22.11 |
| 7,121,336 | B2 * | 10/2006 | Hatley | B08B 9/043 15/104.2 |
| 8,157,919 | B2 | 4/2012 | Vazales et al. | |
| 2003/0209258 | A1 | 11/2003 | Morejon | |
| 2004/0092956 | A1 | 5/2004 | Liddicoat et al. | |
| 2007/0038226 | A1 * | 2/2007 | Galdonik | A61B 17/22 606/114 |
| 2007/0293812 | A1 | 12/2007 | Wright et al. | |
| 2009/0049627 | A1 * | 2/2009 | Kritzler | A61B 1/122 15/104.05 |
| 2010/0306954 | A1 * | 12/2010 | Coscarella | A47L 5/36 15/339 |
| 2011/0023885 | A1 | 2/2011 | Vazales et al. | |
| 2011/0106019 | A1 * | 5/2011 | Bagwell | A61B 1/018 604/267 |
| 2011/0186052 | A1 | 8/2011 | Morejon | |

FOREIGN PATENT DOCUMENTS

| | | |
|---|---|---|
| WO | WO 94/03226 A1 | 2/1994 |
| WO | WO 2009125387 * | 10/2009 |
| WO | WO 2011/126812 A1 | 10/2011 |
| WO | WO 2011126812 * | 10/2011 |

OTHER PUBLICATIONS

Co-pending U.S. Appl. No. 14/026,157, filed Sep. 13, 2013, by Bagwell et al. for "Self Positioning Tracheal Tube Clearance Mechanism Using Skives.".

* cited by examiner

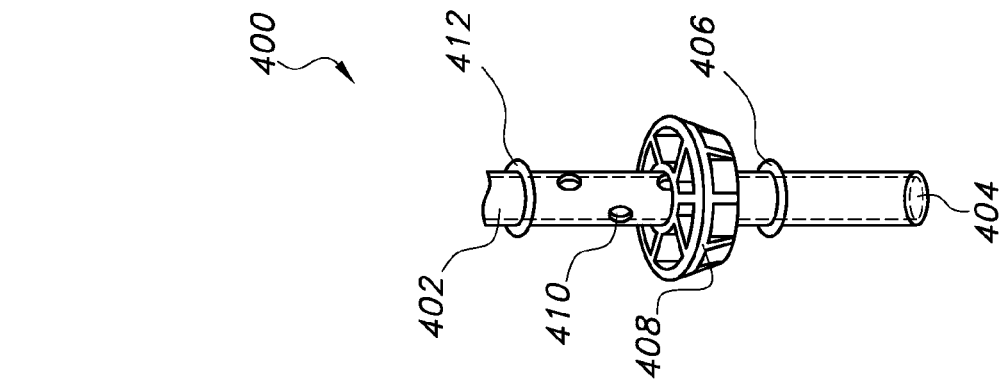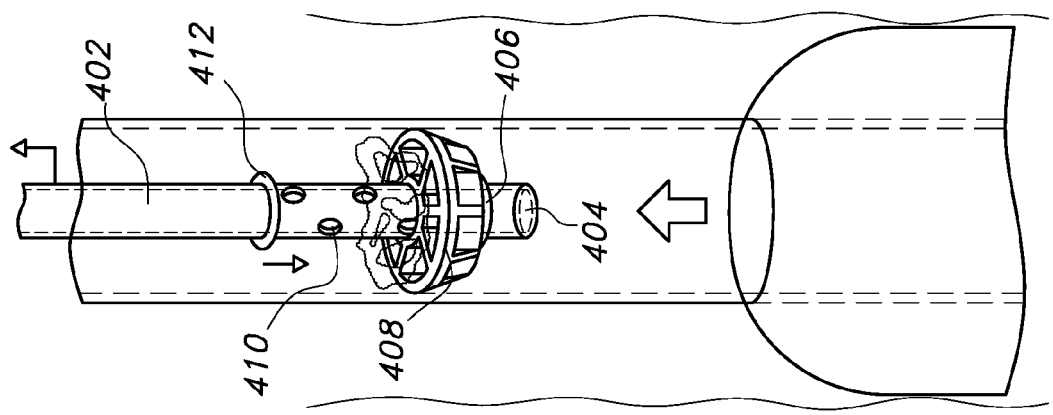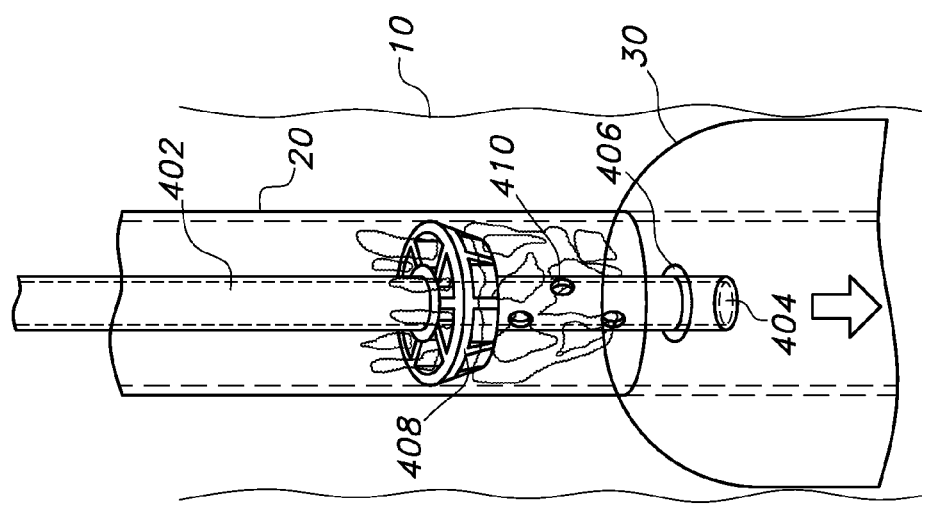

SELF POSITIONING TRACHEAL TUBE CLEARANCE MECHANISM USING A COLLAR

The present disclosure relates to cleaning mechanisms for the central (breathing) lumen of tracheal tubes.

Tracheal intubation involves the insertion of a hollow tubular device, known as a tracheal tube, into the trachea of a patient. The tube may be inserted through the mouth or, less desirably, the nose or may be inserted through the neck by way of an incision in the front of the throat. If inserted through the mouth or nose the tube is referred to as an endotracheal tube, if through the front of the throat the tube is referred to as a tracheostomy or trach tube. The two types of tubes will be referred to as tracheal tubes herein. The tracheal tube passes into the trachea and terminates at a position above the carina, anterior to a position between the second and fourth thoracic vertebrate. Gases may then be introduced through the central lumen of the tracheal tube and into the lungs of the patient.

The primary purpose of tracheal intubation is to mechanically ventilate the patient's lungs when the patient is incapable of normal breathing induced ventilation. Intubation may also be used to apply anesthetic gases during surgical intervention. It is desirable to seal the passageway around the tracheal tube in order to maintain enough air pressure to force the air into the lungs during mechanical ventilation and to prevent escape of gases past the tube (i.e. "short circuiting" or bypassing of the lungs). Such a seal may be produced by the use of an inflatable cuff or balloon surrounding the tracheal tube near its distal end. When the tracheal tube has been introduced into the patient's trachea, the inflatable cuff will normally be located about 3 to 5 centimeters above the carina and within the tube-like trachea.

Once inflated, the cuff will engage the wall of the trachea and thereby seal the trachea and prevent the gases being introduced through the tracheal tube from simply reversing course after exiting the distal end of the tube and traveling back up and around the tube to exit the mouth. While treatment of this sort has proved successful for patients having chronic or acute respiratory diseases, there is a constant risk of several complications.

One of the most common complications in mechanical ventilation is known as ventilator associated (or acquired) pneumonia or VAP. Patients receiving tracheal intubation sometimes develop this pneumonia from an infection of the lungs, possibly induced by contaminated secretions, mucus or biofilm entering the trachea and the lungs after growing in the warm, moist environment in the central lumen of the tracheal tube. Removing these secretions from the tracheal tube lumen would likely reduce the risk of such infections.

In addition, it has been reported that extubated endotracheal tubes had significantly decreased luminal volume and radius compared to unused tubes. Even small changes in the luminal radius result in large changes in resistance to airflow-leading to an increased work of breathing, difficulty in breathing and increased length of hospital stays. The build-up of tenacious secretions within the tracheal tube can lead to difficulty in weaning off the mechanical ventilator, the need for emergency tracheal tube replacement, or the need for tracheostomy, all of which place the patient at greater risk of additional complications.

A number of attempts have been made to develop cleaning mechanisms for the central lumen of tracheal tubes. UK patent application GB 2482618 to Airway Medix Spolka Z.O.O. discusses a cleaning device having a balloon on the distal end and having a source of pressurized liquid and a source of suction to wash the interior of the central lumen and remove the liquid and biofilm. U.S. Pat. No. 8,157,919 to Endoclear LLC provides a medical tube cleaning apparatus with a mechanically actuated, non-inflatable cleaning member. No liquid or suction are used.

What is needed is a mechanism for thorough cleaning of the central tracheal tube lumen.

SUMMARY

This disclosure relates to a device (cleaning device, self-positioning cleaning device, or self-positioning tracheal tube cleaning device) for cleaning the interior walls of the breathing lumen, e.g., a catheter or a tracheal tube. The device has a cleaning lumen and a non-inflatable removal element having a first location on a cleaning lumen or catheter and a second location. The removal element comprises a sliding collar.

The sliding collar changes location axially along the cleaning lumen between two stops that are fixed to the cleaning lumen. The collar can change its overall radial dimensions so that the collar is capable of being in proximity to the cleaning lumen when compressed, but having components that are distanced away from the cleaning lumen when unconstrained. The collar self-positions the device concentrically within the tracheal tube. Suction is desirably applied to the cleaning lumen during use.

BRIEF DESCRIPTION OF THE DRAWINGS

FIG. 1 is a drawing of a cleaning device with its collar against a proximal stop on the cleaning lumen as the cleaning device moves within a catheter, e.g. tracheal tube towards the distal end of the catheter, as indicated by the arrow.

FIG. 2 shows the cleaning device of FIG. 1 with its collar against a distal stop within the catheter as the cleaning device moves away from the distal end of the tracheal tube, as indicated by the arrow. The collar contacts the inner wall of the catheter as the device moves away from the distal end of the catheter . . . .

FIG. 3 shows an embodiment of the cleaning device of FIGS. 1 and 2 outside a tracheal tube. The collar of the device is outside of and around the cleaning lumen. The cleaning lumen has suction ports and proximal and distal stops. The stops define at least two locations of the collar with respect to the cleaning lumen, a first location against the proximal stop and a second location against the distal stop . . . . The cleaning lumen, port, stops, collar and lateral openings are clearly visible.

DETAILED DESCRIPTION

Figure 4:
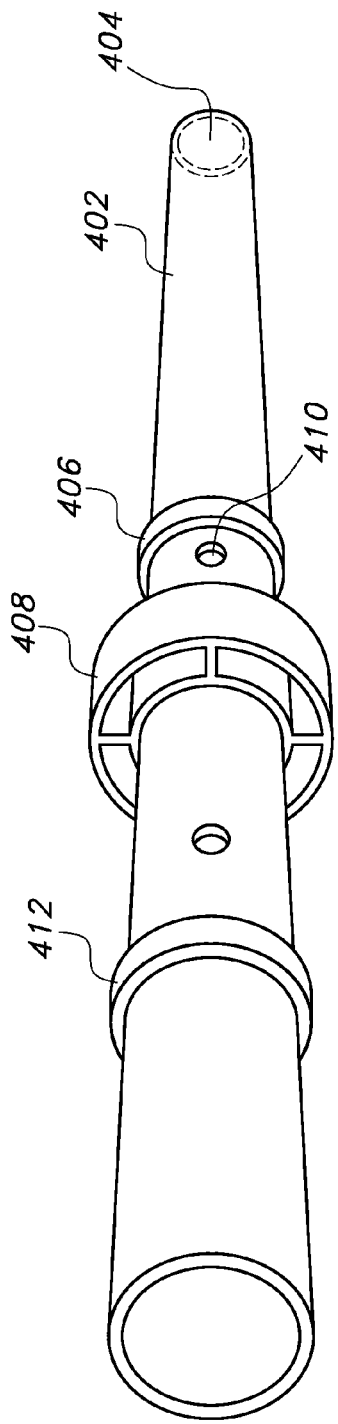
FIG. 4 shows another cleaning device outside a tracheal tube.

Reference will now be made in detail to one or more embodiments, examples of which are illustrated in the drawings. It should be understood that features illustrated or described as part of one embodiment may be used with another embodiment to yield still a further embodiment.

Suction catheters are well known and widely commercially available for many medical uses. Suctioning may be performed using an "open" or "closed" system. In the open system, the suction catheter is merely a flexible plastic tube that is inserted into the tracheal tube breathing lumen with a source of suction connected to the proximal end of the suction catheter. Anything that the suction catheter touches before entering the lumen is preferably maintained in a sterile condition so a "sterile field" is created on or next to the patient. The suction catheter must be carefully handled after it is used since it will be coated with the patient's secretions. In contrast, in the "closed" system, for example that disclosed in U.S. Pat. No. 4,569,344, a device which may be used to suction secretions is enclosed within a generally cylindrical plastic bag to eliminate or minimize contamination of the suction catheter prior to use. This is generally referred to as a "closed suction catheter" and is available under the trade name TRACH CARE® (BALLARD® Medical Products) from Kimberly-Clark Corporation.

Disclosed is a device that enters the tracheal tube either by opening the ventilation circuit or by entering through an opening that gives access to the tracheal tube. The device has a proximal end, a distal end, and the removal element between these ends. The distal end of the device enters the tracheal tube first. The device may contain markings which indicate its advancement through the tracheal tube and may convey to the user information about the location of the device, e.g., when the distal end of the device reaches the distal end of the tracheal tube. The cleaning lumen must of course be smaller than the interior diameter of the tracheal tube. The removal element must deform to fit within the interior of the tracheal tube. The collar is made with at least some components of resilient materials that allow the overall shape of the collar to change from its unconstrained dimensions, when the collar assumes a first position where all the components are maximally extended, to a second position when the collar reversibly deforms during insertion into the interior of the tracheal tube, and to another second position within the tracheal tube when the resilient components adjust their dimensions to compressively fit within the space defined by the interior of the tracheal tube. Regardless of the positions of the collar, i.e., second positions when compressed or the first position when unconstrained, the collar slides along the cleaning lumen between the stops. The collar typically has a first location on a cleaning lumen as the cleaning lumen catheter advances within the catheter and a second location as the cleaning lumen retracts in response to the collar contacting the stops. Intermediate locations of the collar on the cleaning lumen occur between the first and second locations when the cleaning lumen is changing movement on the axial direction within the tracheal tube.

Suction is desirably applied to the cleaning lumen during use.

The removal element self-positions the device to be generally concentric with the tracheal tube when the cleaning lumen is within the tracheal tube. This self-positioning is caused by the bias of the resilient components of the collar, their maximum dimensions when in the first position, and the radial dimensions of the cleaning lumen and the tracheal tube interior.

The removal element has a maximum radial dimension in the first position. In second positions the removal element has its largest radial dimension less than the maximum of the first position. This change occurs in response to constraining forces applied to the collar, e.g., within the tracheal tube; this change allows the cleaning device to fit through openings that are smaller than the maximum radial dimension of the removal element. The transition (change) between the first and second positions is repeatedly reversible.

In the conventional use of an endotracheal tube, air is delivered to the patient's lungs through the breathing channel or lumen inside the tube 20. The tube 20 has a balloon cuff 30 that desirably seals against the trachea 10 such that secretions above the cuff and outside the tube do not move downwardly into the lungs (FIG. 1). Further discussion of the functioning to the balloon cuff may be found, for example, in U.S. Pat. No. 6,802,317 to Goebel. Mucus may nevertheless build up within the breathing channel or lumen of the tube, causing a decrease in the cross-sectional area of the lumen, thus increasing the resistance to air flow within the lumen and so decreasing the air flow to the patient's lungs. The mucus may also harbor unwanted bacteria that may thrive in the warm, moist environment inside the tube.

FIG. 1 shows a self-positioning tracheal tube cleaning device 400 advancing within a tracheal tube, as indicated by the arrow. The cleaning device 400 may be a modified closed suction catheter as described above. The cleaning device 400 wipes the interior of the tracheal tube and removes secretion build-up every time it is used. This device 400 has a distal port 404 on the distal end of the cleaning lumen 402 and lateral ports 410 that are in fluid communication with the interior of the cleaning lumen. The device 400 has a removal element that is a shape adjusting collar 408 that is concentrically positioned on the cleaning lumen 402 and can slide on the cleaning lumen 402. A distal stop 406 and a proximal stop 412 are on the cleaning lumen 402 and the collar 408 is between the stops; the stops restrict the collar 408 to move only between the stops 406, 412.

The collar 408 has proximal and distal ends that are respectively closest to the proximal and distal stops. The proximal end of collar 408 is desirably wider than the distal end as is clearly visible in FIG. 3. The collar 408 has an outer annular ring 416 with maximum radial dimensions when in the first position. The maximum radial dimension of the ring 416 approximately matches or is slightly larger than the cross-sectional internal diameter of the tracheal tube. The annular ring 416 may be continuous or discontinuous. The annular ring 416 has a proximal surface with a first circumference and a distal surface with a second circumference and the second circumference is less than the first circumference. A support network 418, such as struts, rings, spokes, webbing, mesh, etc., connects to the annular ring 416 and is configured to bias the annular ring 416 to extend outwardly to its maximum dimensions in the absence of constraining forces. The support network 418 also connects to at least one cuff 420 that encircles the cleaning lumen 402 and the cuff 420 is the component of the collar 408 that is closest to the cleaning lumen 402 in the absence of constraining forces.

The support network 418 is biased to reversibly deflect outward, away from the exterior surface of the cleaning lumen 402 in the absence of constraining forces. The distance that is spanned by the support network 418 between the annular ring 416 and cuff 420 is longer than the radial distance between the exterior surface of the cleaning lumen 402 and the interior of the tracheal tube when the cleaning lumen 402 is concentric within the tracheal tube. An embodiment of the support network 418 has a bending region 422 that attaches to the cuff 420 and it has an intermediate portion 424 between the bending region 422 and the connection to the annular ring 416; other embodiments omit the intermediate portion.

The cuff 420 is relatively inflexible; i.e. its dimensions remain essentially fixed regardless of advancement or retraction of the collar 408 within the tracheal tube between the stops 406, 412. When subjected to constraining forces, however, the bending region 422 of the support network 418 and the annular ring 416 can reversibly deform and/or deflect so that the collar 408 can fit through an opening that is no more than about 150% of the cross-sectional area defined by the exterior of the cleaning lumen 402 and is no more than 80% of the cross-sectional area defined by the interior of the tracheal tube. When the device is advanced within the tracheal tube, the support network 418 is configured to allow reversible flexing or deflection towards the exterior surface of the cleaning lumen 402 in the direction opposite the advancement. Such reversible flexing can deform the annular ring 416 so that the maximum radial dimension of the ring within the tracheal tube can shift in response to constraining and frictional forces encountered between the ring and the interior wall of the tracheal tube. The flexing can shift maximum radial dimensions of the ring to change between the proximal and distal surfaces of the ring 416. The first position is found when the collar is outside of the tracheal tube and second positions exist when the collar is within the tracheal tube.

When the device is retracted within the tracheal tube, the bias of the support network 418 tends to hold the annular ring 416 in an expanded state where the annular ring 416 strives to attain maximum radial dimensions within the tube. During retraction the ring 416 is in close proximity or contacts the interior wall of the tracheal tube so the collar can dislodge any deposits of mucus 40, secretions, etc. that protrude into the interior of the tracheal tube. The annular ring 416 can have a portion that collects such deposits or the support network 418 can have a portion that collects such deposits, or these portions can both collect such deposits.

FIG. 2 shows the cleaning device 400 being retracted within the tracheal tube, as indicated by the arrow. The collar 408 contacts the inner walls of the tube as described above, as the device 400 moves away from the distal end of the tube, loosening any deposits and collecting them. The lateral openings 410 are in fluid communication with the interior of the cleaning lumen 402. Suction applied to the proximal end (not shown) of the cleaning lumen 402 pulls the deposits into the cleaning lumen 402 through the lateral openings 410 as the collar approaches each of the lateral openings 410. The collar 408 should be able to move freely between the two stops 406, 412.

Figure 5:
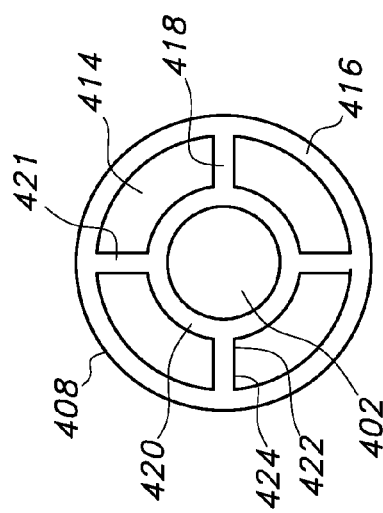
FIG. 5 shows a cross-sectional view of the collar of the device of FIG. 4 and optional air channels in the collar.

FIG. 3 shows the cleaning device 400 outside of the tracheal tube. The cleaning lumen 402, distal port 404, stops 406, 412, collar 408 and lateral openings 410 are clearly visible. FIG. 4 shows another view of another embodiment of a cleaning device 400. FIG. 5 shows a cross-sectional view of the collar 408 of the device shown in FIG. 4. The air channels 414 are optional for this and other embodiments.

While the present disclosure has been described in connection with certain preferred embodiments it is to be understood that the subject matter encompassed by way of the present disclosure is not to be limited to those specific embodiments. On the contrary, it is intended for the subject matter of the disclosure to include all alternatives, modifications and equivalents as can be included within the spirit and scope of the following claims.

We claim:

1. A device for cleaning the interior wall of a catheter, the device comprising:
   a cleaning lumen having an exterior surface, a proximal end, and a distal end, the cleaning lumen further comprising a distal stop on the cleaning lumen and a proximal stop on the cleaning lumen;
   a collar including
      a cuff encircling the cleaning lumen, and
      an outer annular ring attached to the cuff by a support network, the support network comprising a plurality of struts,
   wherein the cuff is slidable on the exterior surface of the cleaning lumen from a first location to a second location between the distal stop and the proximal stop.

2. The device of claim 1, wherein the support network is biased to reversibly deflect outwardly away from the exterior surface of the cleaning lumen.

3. The device of claim 1, wherein the radial distance that is spanned from the annular ring to the cuff when the device is not within the tracheal tube is longer than the radial distance between the exterior surface of the cleaning lumen and the interior of the tracheal tube when the cleaning lumen is concentric within the tracheal tube.

4. The device of claim 1, wherein the collar can fit through an opening that is no more than about 150% of the cross-sectional area defined by the exterior of the cleaning lumen and is no more than 80% of the cross-sectional area defined by the interior of the catheter.

5. The device of claim 1, wherein suction applied to the proximal end of said cleaning lumen creates suction at the distal end of the lumen.

6. The device of claim 1, further comprising one or more lateral ports between the first and second locations.

7. The device of claim 6, wherein suction applied to the proximal end of said cleaning lumen creates suction at the lateral ports.

8. The device of claim 1, where the collar concentrically positions the device in the interior of the tracheal tube.

9. The device of claim 1, wherein the plurality of struts extend radially and axially with respect to the cleaning lumen.

10. The device of claim 1, wherein a portion of the plurality of struts extend at an angle with respect to the cleaning lumen.

11. A self-positioning device for cleaning the interior wall of a tracheal tube, the device comprising:
    a cleaning lumen having an exterior surface, a proximal end, and a distal end, the cleaning lumen further comprising a distal stop on the cleaning lumen and a proximal stop the cleaning lumen;
    a collar including
       a cuff encircling the cleaning lumen, and
       an outer annular ring attached to the cuff by a support network, the outer annular ring having a proximal surface with a first circumference and a distal surface with a second circumference,
    wherein the cuff is slidable on the exterior surface of the cleaning lumen from a first location to a second location between the distal stop and the proximal stop.

12. The device of claim 11, wherein said second circumference is less than the first circumference.

13. The device of claim 11, wherein the outer annular ring is deformable such that a maximum radial dimension of the outer annular ring shifts between the proximal and distal surfaces.

14. The device of claim 11, wherein the support network is a plurality of struts.

15. The device of claim 14, wherein the plurality of struts extend radially and axially with respect to the cleaning lumen.

16. The device of claim 11, wherein the collar has a first position and a second position, wherein the collar has a maximum radial dimension in the first position, and wherein the collar is radially smaller in the second position than in the first position.

17. The device of claim 16, wherein the outer annular ring and the support network deform to enable the collar to change from the first position to the second position.

18. The device of claim 11, wherein the first location of the collar on the exterior surface of the cleaning lumen is against the proximal stop and the second location of the collar on the exterior surface of the cleaning lumen is against the distal stop.

19. The device of claim 11, wherein the first stop and the second stop restrict the movement of the collar on the cleaning lumen such that the collar moves only between the first stop and the second stop.

\* \* \* \* \*